United States Patent
Kang et al.

(10) Patent No.: US 7,830,505 B2
(45) Date of Patent: Nov. 9, 2010

(54) STRUCTURE FOR DIAGNOSIS SYSTEM OF REACTION PROCESS

(75) Inventors: Sang Woo Kang, Seoul (KR); Ju Young Yun, Seoul (KR); Dae Jin Seong, Chungcheongnam-do (KR); Yong Hyeon Shin, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 278 days.

(21) Appl. No.: 12/222,332

(22) Filed: Aug. 7, 2008

(65) Prior Publication Data
US 2009/0046285 A1    Feb. 19, 2009

(30) Foreign Application Priority Data
Aug. 7, 2007    (KR) .............. 10-2007-0079049
Oct. 10, 2007   (KR) .............. 10-2007-0101765

(51) Int. Cl.
*G01J 3/30* (2006.01)

(52) U.S. Cl. ..................... 356/311
(58) Field of Classification Search ............. None
See application file for complete search history.

(56) References Cited

U.S. PATENT DOCUMENTS
7,598,509 B2 * 10/2009 Ershov et al. ........... 250/504 R
2006/0123884 A1 * 6/2006 Selker et al. ............. 73/24.02

FOREIGN PATENT DOCUMENTS
KR   10-2006-0009668   2/2006

* cited by examiner

*Primary Examiner*—Tu T Nguyen
(74) *Attorney, Agent, or Firm*—Clark & Brody

(57) ABSTRACT

The present invention relates to a spectroscopy analyzer for real-time diagnostics of process, and more particularly, to a spectroscopy analyzer for real-time diagnostics of process, in which a beam is injected to a reaction byproduct or a reactant and then an output beam is measured, thereby performing quantitative and qualitative analysis of the reaction byproduct or the reactant.

23 Claims, 6 Drawing Sheets

STRUCTURE FOR DIAGNOSIS SYSTEM OF REACTION PROCESS

TECHNICAL FIELD

The present invention relates to a spectroscopy analyzer for real-time diagnostics of process, and more particularly, to a spectroscopy analyzer for real-time diagnostics of process, in which a beam is injected to a reaction byproduct or a reactant and then an output beam is measured, thereby performing quantitative and qualitative analysis of the reaction byproduct or the reactant.

BACKGROUND ART

Every atom or molecule moves continuously within a space, and also includes energy corresponding to such movement. Since the energy associated with the movement of the atom or molecule is quantized, the energy can be existed only in a certain energy state. The atom or molecule which moves in the certain energy state may absorb energy from the outside and thus be excited to a high energy state. The energy can be expressed as follows: $E=h\nu$, wherein h is Planck's constant and v is a frequency. Therefore, the energy necessary to be excited to a higher energy state can be expressed as: $\Delta E=h(\nu_2-\nu_1)=h\cdot\Delta\nu$. Since h is the constant, the energy necessary to be excited is a function only of the frequency, and a spectrum which is generated when the atom or molecule absorbs certain energy is a function of the frequency. The energy state of the atom or molecule becomes different according to a kind of the movement, and thus an amount of the energy to be absorbed becomes different. The movement of molecule corresponding to energy of the infrared range includes vibration, rotation and translation. Particularly, the movement associated with the infrared spectrometry is transition due to the vibration and rotation movement. In general, the energy necessary for the vibration is larger than the energy necessary for the rotation. The movement corresponding to mid-infrared range of the infrared range, which is typically used, is the vibration movement. Therefore, the infrared spectrometry is an instrumental analysis method in which information of the molecular vibration-rotation movement is obtained by using a light source for generating light within the mid-infrared range so as to check a molecular structure and also perform the quantitative analysis.

In a conventional spectroscopy analyzer, the quantitative and qualitative analysis of a reaction byproduct or a reactant is performed by injecting a beam to the reaction byproduct or the reactant and then detecting the beam.

In the conventional spectroscopy analyzer, since the spectroscopic analysis is performed in an atmospheric state, it is difficult to exactly perform the spectroscopic analysis of the reaction byproduct or the reactant, and also since the reaction byproduct or the reactant is attached and deposited on an input window through which the beam is introduced, an output window through which the beam is output, a reflecting mirror and so on, the beam may be not smoothly transmitted.

In case that the reaction byproduct or the reactant is attached and deposited on the input window, the output window, a reflecting mirror and so on, maintenance of dissolving and removing the reaction byproduct or the reactant is needed. However, a period of the maintenance is short, and this makes it difficult to perform the real-time diagnostics of process.

Further, in the conventional spectroscopy analyzer, there is another problem that it is difficult to control a temperature of the input window and the output window within a short time so as to be suitable for the reaction byproduct or the reactant which is introduced into a reactor.

DISCLOSURE OF THE INVENTION

It is an object of the present invention to provide a spectroscopy analyzer for real-time diagnostics of process, in which a spectroscopic analysis is performed in vacuum state, whereby it is possible to perform the real-time diagnostics of process, and also which can inform a preliminary maintenance period by monitoring gas discharged from a reactor during a period of off-time.

It is another object of the present invention to provide a spectroscopy analyzer for real-time diagnostics of process, which can prevent contamination of an input window, an output window, a reflecting mirror, a crystal and the like by a reaction byproduct or a reactant, thereby precisely performing the spectroscopic analysis.

It is yet another object of the present invention to provide a spectroscopy analyzer for real-time diagnostics of process, in which the input window, the output window, the reflecting mirror, the crystal and the like are not provided in the reactor connected with an exhaust line, but provided in a chemical reaction chamber that a chemical reaction is occurred, so that quantitative and qualitative analysis with respect to a component of the reaction byproduct or the reactant in the chemical reaction chamber is directly performed.

It is yet another object of the present invention to provide a spectroscopy analyzer for real-time diagnostics of process, in which the input window, the output window, the reflecting mirror, the crystal and the like are provided in the reactor connected with an exhaust line as well as in a chemical reaction chamber that the chemical reaction is occurred, so that the quantitative and qualitative analysis with respect to the component of the reaction byproduct or the reactant in the chemical reaction chamber is performed. In this case, an infrared ray emitting unit for generating infrared ray to be introduced to the input window may be provided at each of the reactor and the chemical reaction chamber. Meanwhile, only a single infrared ray emitting unit may be provided. At this time, the infrared ray emitting unit is rotatably disposed at a predetermined angle so that the infrared ray can be selectively introduced to the reactor or the chemical reaction chamber. Therefore, the two infrared ray emitting units may be provided so as to monitor the reactor and the chemical reaction chamber at the same time, or the single infrared ray emitting unit may be provided so as to selectively monitor the reactor or the chemical reaction chamber.

It is yet another object of the present invention to provide a spectroscopy analyzer for real-time diagnostics of process, which can reduce a level of contamination due to the absorption and deposition of the reaction byproduct or the reactant and thus can extend the maintenance period.

It is yet another object of the present invention to provide a spectroscopy analyzer for real-time diagnostics of process, which can control a temperature of the input window and the output window that are provided to the analyzing chamber according to a temperature of the reaction byproduct or the reactant.

In order to achieve the above objects, the present invention provides a spectroscopy analyzer for real-time diagnostics of process, comprising a reactor 10 of which an internal portion becomes a vacuum state; a detector 20 for detecting a beam output from the reactor 10; and an analyzer 30 for performing quantitative and qualitative analysis of a sample using an intensity of the detected beam, wherein the reactor 10 comprises, an input window 11 through which the beam is introduced; a receiving part 12 in which the beam introduced through the input window 11 is injected, and a reaction byproduct or a reactant is received temporarily so as to perform the real-time diagnostics of the reaction byproduct or the reactant; an output window 13 through which the beam injected in the receiving part 12 is output after being refracted and scattered by the reaction byproduct or the reactant; and a reflecting mirror 14 which is provided in the receiving part, and reflects the beam introduced through the input window 11 to be reciprocated at last once in the receiving part 12 and then outputs the beam.

In the present invention, the reflecting mirror 14 is disposed so that the beam introduced through the input window 11 can be reciprocated along a zigzag-shaped path in the receiving part 12, and the receiving part 12 is formed with a zigzag path for guiding a flow of the reaction byproduct or the reactant along the zigzag-shaped path of the introduced beam, and the reactor 10 further comprises a pressure controller 15 for controlling pressure in the reactor 10. And the spectroscopy analyzer further comprises an air curtain 16 for injecting nitrogen gas so as to prevent the reaction byproduct or the reactant from being attached and deposited on the input window 11, the output window 13 or the reflecting mirror 14, and a temperature of the reactor 10 can be controlled. Also, an injecting port 17 for injecting gas or liquid so as to clean the sample attached and deposited on the input window 11, the output window 13 or the reflecting mirror 14 may be further provided.

The present invention provides a spectroscopy analyzer for real-time diagnostics of process, comprising: a reactor 110 of which an internal portion becomes a vacuum state; a detector 120 for detecting refraction and scatter of a beam output from the reactor 110; and an analyzer 130 for performing quantitative and qualitative analysis of a sample using an intensity of the detected beam; wherein the reactor 110 comprises, an input window 111 through which the beam is introduced; a receiving part 112 in which the beam introduced through the input window 111 is injected, and a reaction byproduct or a reactant is received temporarily so as to perform the real-time diagnostics of the reaction byproduct or the reactant; a crystal 114 which is fixedly provided in the receiving part 112 by a fixing part 113 so that the beam refracted and scattered by the reaction byproduct or the reactant can be passed therethrough; a plasma electrode 115 which is disposed to be apart from the crystal 114 and provides continuous radiant rays in a far-infrared range; and an output window 116 which outputs the beam output from the crystal 114. The present invention may further comprises a reflecting mirror M which is provided in the receiving part 112 so that the beam input through the input window 111 is reciprocated at least once in the crystal 114 and then output through the output window 116.

In the present invention the reactor 110 further comprises a pressure controller 117 for controlling pressure in the reactor 110, and a cleaning port 118 for injecting inert gas so as to prevent attachment and deposition of the reaction byproduct or the reactant on the crystal 114 and the plasma electrode 115. The fixing part 113 can control a temperature of the crystal 114, and the reactor 110 further comprises an injecting port 119 for injecting gas or liquid so as to clean the sample attached and deposited on the crystal 114 and the plasma electrode 115, which is provided between the crystal 114 and the plasma electrode 115, and the analyzer analyzes gas discharged from the reactor during a period of off-time and informs a cleaning period or a preliminary maintenance period.

Meanwhile, the spectroscopy analyzer for real-time diagnostics of process may further comprise a first gas receiving part 1110 is formed at an outer surface of the reactor 1130 so as to include a portion that the input window 1131 is provided, so that, when gas is injected into the first gas receiving part 1110, the injected gas can be contacted with the outer surface of the input window 1131; and a second gas receiving part 1120 is formed at an outer surface of the reactor 1130 so as to include a portion that the output window 1132 is provided, so that, when the gas is injected into the second gas receiving part 1120, the injected gas can be contacted with the outer surface of the output window 1132.

Further, the first gas receiving part 1110 and the second gas receiving part 1120 are communicated with each other, and the spectroscopy analyzer further comprises an gas receiving part input window 1111 which is provided in the first gas receiving part 1110 so that a beam generated from an outside of the first gas receiving part 1110 can be injected into the first gas receiving part 1110, and then be introduced through the input window 1131; and an gas receiving part output window 1122 which is provided in the second gas receiving part 1120 so that the beam output through the output window 1132 can be output to an outside of the second gas receiving part 1120. And the first gas receiving part 1110 and the second gas receiving part 1120 are communicated with each other through lower ends thereof so that a recessed portion is formed between the first gas receiving part 1110 and the second gas receiving part 1120, and the reactor 1130 is detachably disposed at the recessed portion.

The present invention may further comprise a gas outlet valve 1162 which is connected to the first gas receiving part 1110 and the second gas receiving part 1120; and a pump 1160 which is connected to the first gas receiving part 1110 and the second gas receiving part 1120 via the gas outlet valve 1162, and also further comprises a gas supplying part 1150 for supplying gas in the first gas receiving part 1110 and the second gas receiving part 1120; and a temperature control part 1154 for controlling a temperature of the gas in the gas supplying part 1150. And a volume of one or all of the first gas receiving part 1110 and the second gas receiving part 1120 can be controlled, and at least one of the first gas receiving part 1110 and the second gas receiving part 1120 has a length adjuster for adjusting a length thereof.

Meanwhile, the present invention provides a spectroscopy analyzer for real-time diagnostics of process, comprising a chemical reaction chamber in which a chemical reaction is occurred; an input window which is provided at the chemical reaction chamber and through which a beam is introduced; a crystal which is fixedly provided in the chemical reaction chamber by a fixing part so that the beam refracted and scattered by a reaction byproduct or a reactant in the chemical reaction chamber is passed therethrough; a plasma electrode which is disposed to be apart from the crystal and provide continuous radiant rays in a far-infrared range; an output window which is provided in the chemical reaction chamber so as to output the beam from the crystal; a reflecting mirror which is provided in the chemical reaction chamber so that the beam input through the input window is reciprocated at least once in the crystal and then output through the output window.

a detector for detecting refraction and scatter of the beam output from the chemical reaction chamber; and an analyzer for performing quantitative and qualitative analysis of a sample using an intensity of the detected beam.

Figure 1:
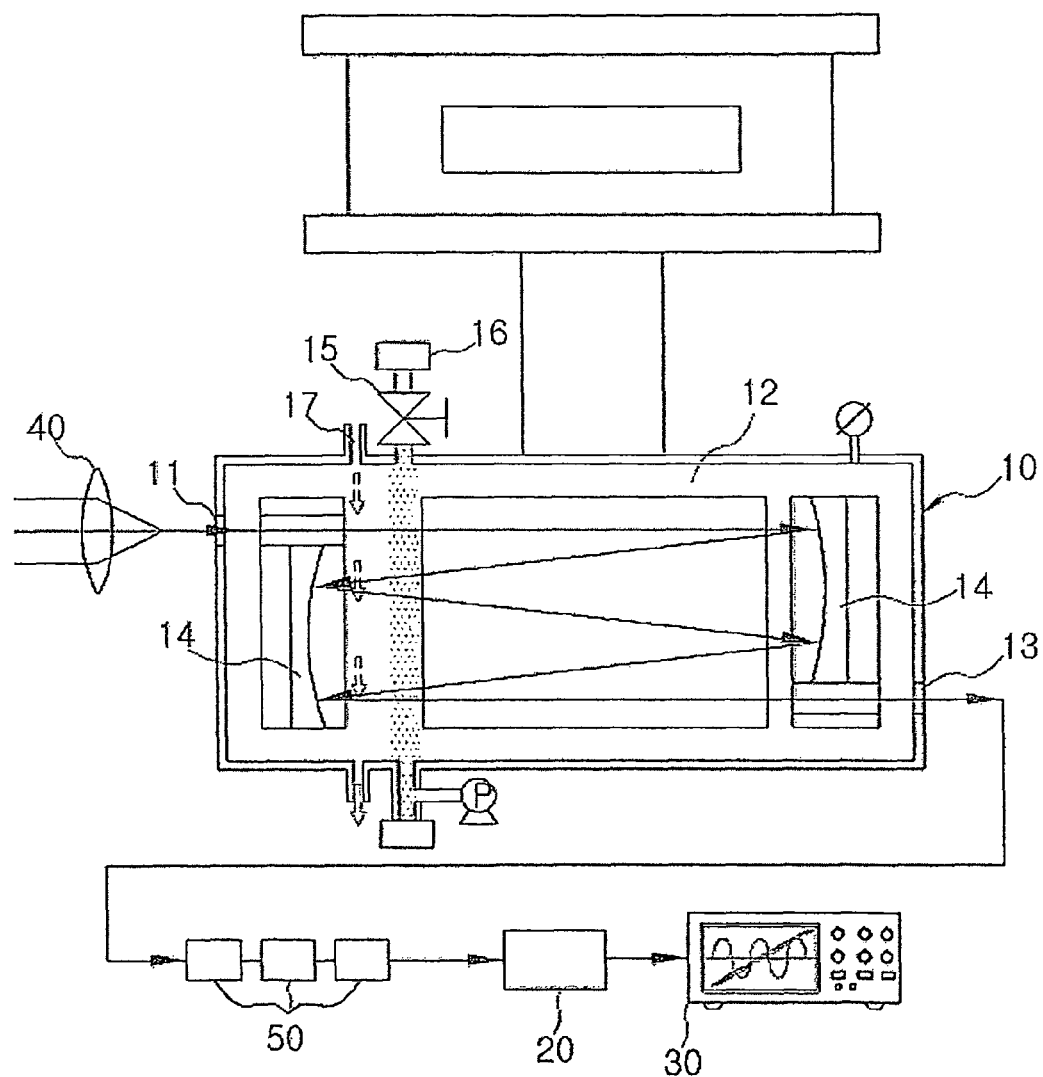
FIG. 1 is a schematic diagram of an infrared spectroscopy analyzer for real-time diagnostics of process according to the present invention.

DETAILED DESCRIPTION OF MAIN ELEMENTS 10, 110: reactor 11, 111: input window
12, 112: receiving part 13, 116: output window
14: reflecting mirror 15, 117: pressure controller
16: air curtain 17, 119: injecting port
20, 120: detector 30, 130: analyzer
113: fixing part 114: crystal
115: plasma electrode 118: cleaning port
1110: first gas receiving part
1111: gas receiving part input window
1113: length adjuster
1120: second gas receiving part
1122: gas receiving part output window
1123: length adjuster
1130: reactor 1131: input window
1132: output window
1150: gas supplying part
1151: gas inlet valve
1154: temperature control part
1160: pump 1162: gas outlet valve
1200: infrared ray emitting unit
1300: infrared ray receiving unit
1400: calculating unit
1110a: first gas receiving part
1111a: gas receiving part input window
1120a: second gas receiving part
1222a: gas receiving part output window
1130a: reactor 1131a: input window
1132a: output window

BEST MODE FOR CARRYING OUT THE INVENTION

Practical and presently preferred embodiments of the present invention are illustrative as shown in the following Examples and Comparative Examples.

However, it will be appreciated that those skilled in the art, on consideration of this disclosure, may make modifications and improvements within the spirit and scope of the present invention.

FIG. 1 is a schematic diagram of an infrared spectroscopy analyzer for real-time diagnostics of process according to the present invention.

As shown in the drawing, the infrared spectroscopy analyzer for real-time diagnostics of process according to the present invention includes a reactor 10 which is provided with an input window 11, a receiving part 12, an output window 13 and a reflecting mirror 14 and of which an interior portion is in a vacuum state; a detector 20 which detects refraction and scatter of a beam output from the reactor 10; and an analyzer 30 which performs quantitative and qualitative analysis of a sample using an intensity of the detected beam.

The reactor 10 has the input window 11, the receiving part 12, the output window 13 and the reflecting mirror 14, and the interior portion thereof is in a vacuum state. A reaction byproduct or a reactant is put in the reactor 10, and then a beam is injected to the reaction byproduct or the reactant. Further, the reactor 10 further includes a pressure controller 15 for controlling pressure in the reactor 10, and thus it is possible to perform a measuring process in an optimum pressure range.

The input window 11 is provided at the reactor 10 so that the beam can be introduced therethrough.

The receiving part 12 temporarily receives the reaction byproduct or the reactant so as to perform the real-time analysis of the reaction byproduct or the reactant. Also, the beam that is introduced through the input window 11 is injected into the receiving part 12. At this time, the injected beam is refracted and scattered by the reaction byproduct or the reactant. And by measuring an intensity of the refracted and scattered beam, the quantitative and qualitative analysis of the sample can be performed. Since the exhaust gas and the like discharged from an exhaust port is temporarily received in the receiving part 12 and then discharged after the spectroscopic analysis, it is possible to perform the real-time diagnostics of process. Further, the receiving portion 12 may be directly inserted into the exhaust port so as to perform the real-time diagnostics of process as shown in FIG. 1. Alternatively, the exhaust port may have other small port through which the reaction byproduct or the reactant is collected or sampled so as to perform the real-time diagnostics of process.

Referring to FIG. 1, the reflecting mirror 14 is disposed so that the beam introduced through the input window 11 is reciprocated along a zigzag-shaped path in the receiving part 12. That is, the reflecting mirror 14 is disposed so that the beam introduced through the input window 11 is reciprocated at least once within the receiving part 12 and then output through the output window 13. To this end, two mirrors may be respectively arranged around the input window 11 and the output window 13, and each of the two mirrors may be a concave mirror or a plane mirror. In case of the plane mirror, the mirror is disposed inclinedly at a predetermined angle so as to form the zigzag-shaped path of the introduced beam. Since the beam introduced in the receiving part 12 forms the zigzag-shaped path, a detection distance of the beam is extended and thus measuring sensitivity is increased.

Figure 2:
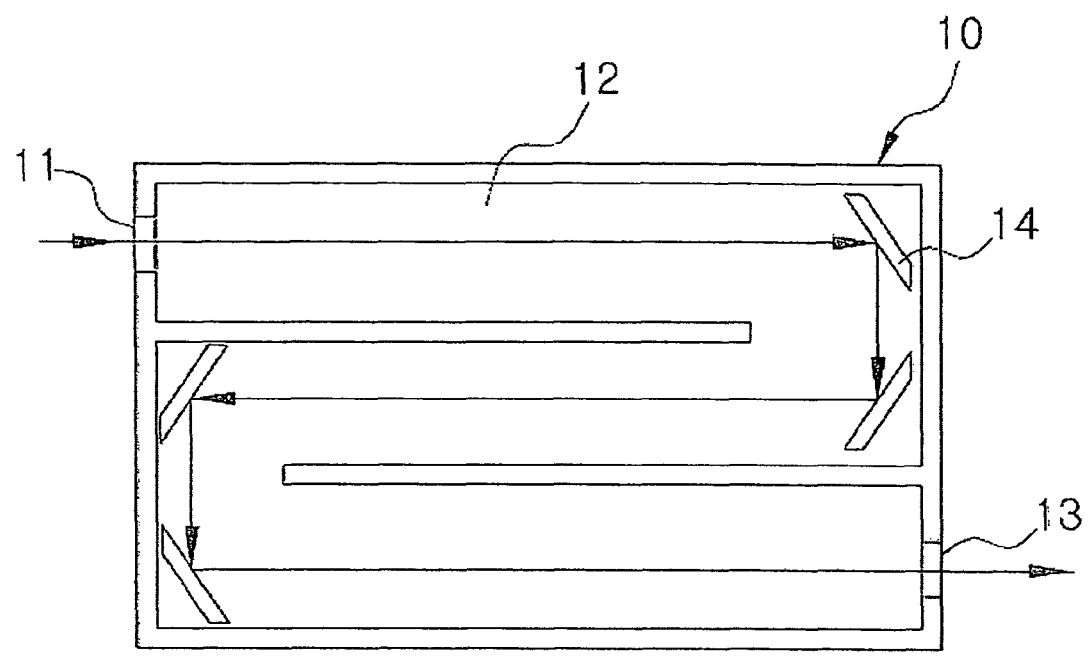
FIG. 2 is a schematic diagram of another type reactor of the present invention.

Meanwhile, referring to FIG. 2, the receiving part 12 may be formed with other zigzag path for guiding a flow of the reaction byproduct or the reactant. In this case, the zigzag path formed in the receiving part 12 includes the zigzag-shaped path of the beam introduced in the receiving part 12. Therefore, the path of the beam is extended, and also the paths for the beam and the reaction byproduct or the reactant are formed in the same direction.

The beam introduced in the receiving part 12 is passed through the reaction byproduct or the reactant and then discharged through the output window 13.

The detector 20 functions to detect the refraction and scatter of the beam output from the reactor 10. The detector 20 includes an IR detector like MCT.

The analyzer 30 performs the quantitative and qualitative analysis of a sample using an intensity of the beam detected by the detector 20.

Figure 3:
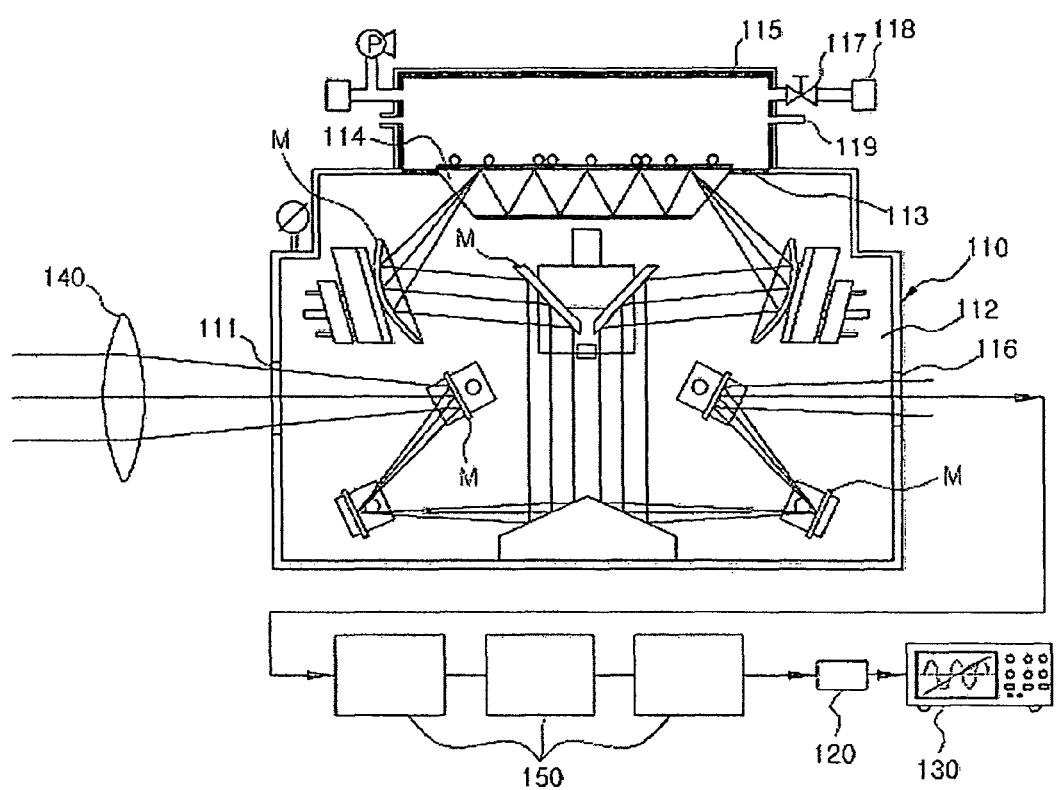
FIG. 3 is a schematic diagram of an infrared spectroscopy analyzer for real-time diagnostics of process according to another embodiment of the present invention.

FIG. 3 is a schematic diagram of an infrared spectroscopy analyzer for real-time diagnostics of process according to another embodiment of the present invention.

As shown in the drawing, another type spectroscopy analyzer for real-time diagnostics of process according to the present invention includes a reactor 110 which is provided with an input window 111, a receiving part 112 for temporarily receiving a reaction byproduct or a reactant, a crystal 114 which is fixedly installed in the receiving part 112 by a fixing part 113 and also through which a beam refracted and scattered by the reaction byproduct or the reactant is passed, a plasma electrode 115 which is disposed to be apart from the crystal 114, and an output window 116; a detector 120 which detects refraction and scatter of a beam output from the reactor 110; and an analyzer 130 which performs quantitative and qualitative analysis of a sample using an intensity of the detected beam.

The reactor 110 has the input window 111, the receiving part 112, the output window 116, the crystal 114 and the plasma electrode 115, and an interior portion of the reactor 110 is in a vacuum state. The beam introduced in the reactor 110 is refracted and scattered by the reaction byproduct or the reactant and then output to the outside of the reactor 110. Further, like in the previous infrared spectroscopy analyzer for real-time diagnostics of process according to the present invention, the reactor 110 further includes a pressure regulator 117 for controlling pressure in the reactor 110, and thus it is possible to perform a measuring process in an optimum pressure range.

The input window 111 and the output window 116 have the same functions as those in the previous infrared spectroscopy analyzer for real-time diagnostics of process according to the present invention.

In the receiving part 112, the beam input through the input window 111 is introduced and also the reaction byproduct or the reactant is temporarily received so as to perform the real-time analysis of the reaction byproduct or the reactant.

The crystal 114 is fixedly disposed in the receiving part 112 by the fixing part 113, so that the beam introduced in the receiving part 112 is passed through the crystal 114 before the beam is refracted and scattered by the reaction byproduct or the reactant and then output to the outside of the receiving part 112. Meanwhile, referring to FIG. 3, a reflecting mirror M for reflecting the beam may be provided in the receiving part 112 so that the beam input through the input window 111 is reciprocated at least once in the crystal 114 and then output through the output window 116. In addition, it is preferred that the fixing part 113 can control a temperature of the crystal 114.

The plasma electrode 115 is disposed to be apart from the crystal 114 and functions to promote cleaning of the crystal 114 or dissolution of the reaction byproduct or the reactant or other foreign substances attached and deposited on the crystal 114.

Preferably, in order to prevent the reaction byproduct or the reactant from being attached and deposited on the crystal 114 and the plasma electrode 115, a cleaning port 118 for injecting nitrogen gas is further provided. Also, in order to clean the sample attached and deposited on the crystal 114 and the plasma electrode 115, it is preferred that an injecting port 119 for injecting gas or liquid between the crystal 114 and the plasma electrode 115 is further provided.

And the detector 120 and the analyzer 130 are the same as those in the previous infrared spectroscopy analyzer for real-time diagnostics of process according to the present invention.

Reference numerals 40 and 140 designate a focus lens, and 50 and 150 are a focus lens and a flat mirror.

Although not shown in drawings, in another embodiment of the present invention, the input window, output window, reflecting mirror, the crystal and so on may be not provided in the reactor connected with an exhaust line, but provided in a chemical reaction chamber that a chemical reaction is occurred. Thus, quantitative and qualitative analysis with respect to a component of the reaction byproduct or the reactant in the chemical reaction chamber is directly performed. Particularly, the mirror is disposed so that the beam introduced through the input window is impacted at least once to an internal wall of the chemical reaction chamber and then output through the output window, thereby monitoring a status of the internal wall of the chemical reaction chamber.

Although not shown in drawings, in yet another embodiment of the present invention, the input window, the output window, the reflecting mirror, the crystal and the like are provided in the reactor connected with an exhaust line as well as in a chemical reaction chamber that the chemical reaction is occurred. Thus, the quantitative and qualitative analysis with respect to the component of the reaction byproduct or the reactant in the chemical reaction chamber is performed directly. In this case, an infrared ray emitting unit for generating infrared ray to be introduced through the input window may be provided at each of the reactor and the chemical reaction chamber. Meanwhile, only a single infrared ray emitting unit may be provided. At this time, the infrared ray emitting unit is rotatably disposed at a predetermined angle so that the infrared ray can be selectively introduced to the reactor or the chemical reaction chamber. Therefore, the two infrared ray emitting units may be provided so as to monitor the reactor and the chemical reaction chamber at the same time, or the single infrared ray emitting unit may be provided so as to selectively monitor the reactor or the chemical reaction chamber.

Figure 4:
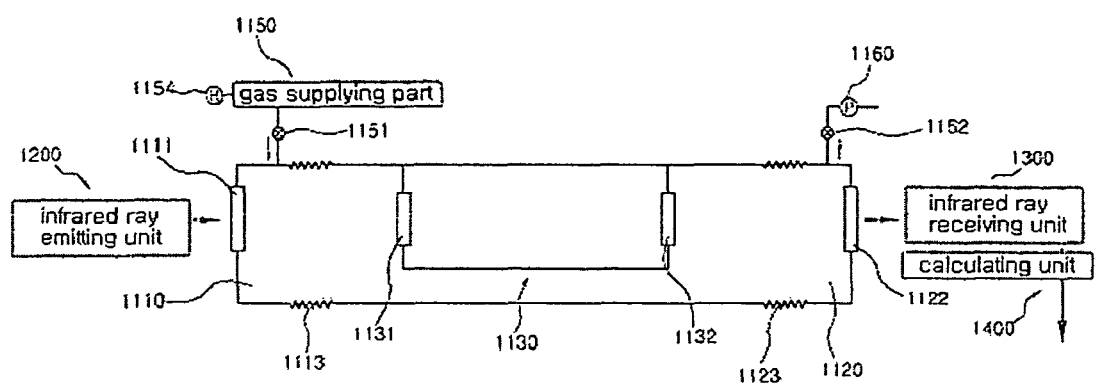
FIG. 4 is a schematic diagram of a spectroscopy analyzer for real-time diagnostics of process according to another embodiment of the present invention.
Figure 5:
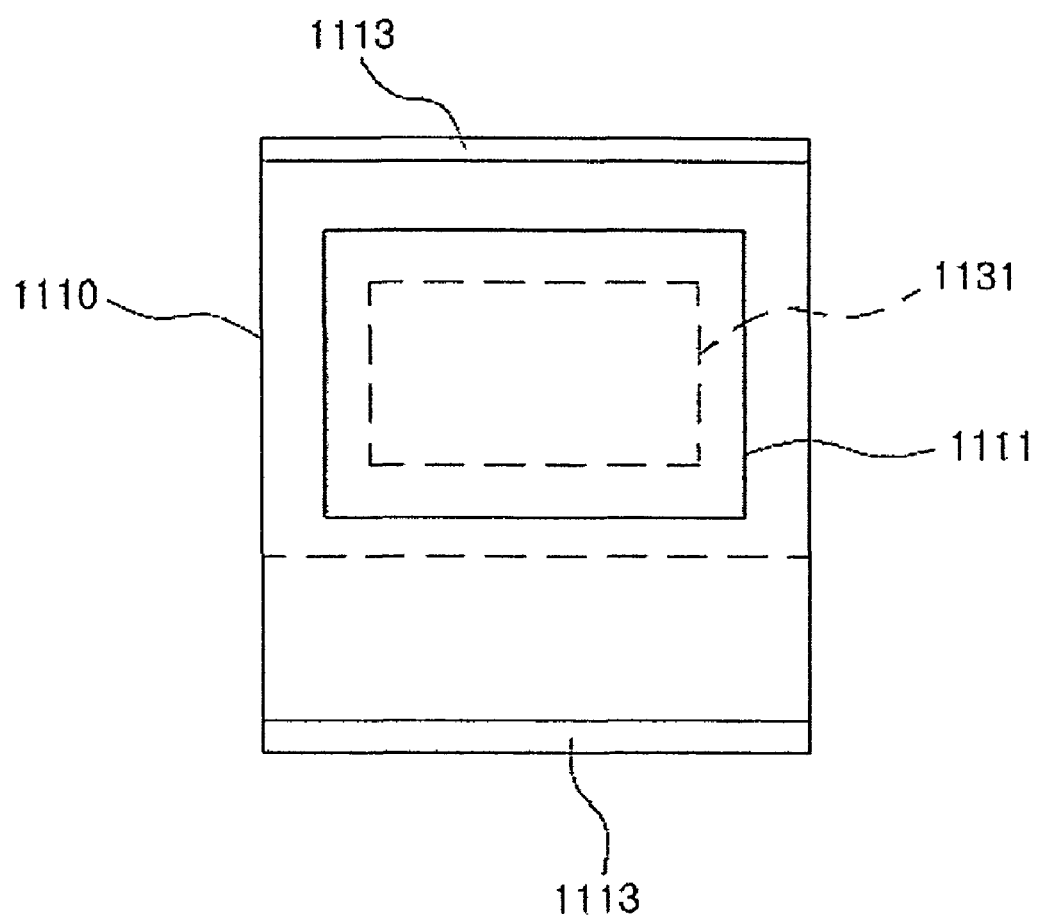
FIG. 5 is a schematic left side view of a main part of FIG. 4.
Figure 6:
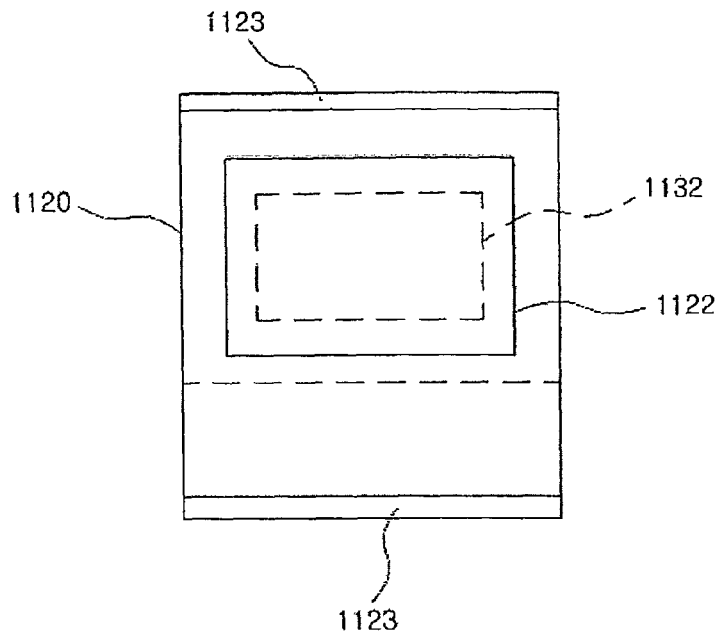
FIG. 6 is a schematic right side view of the main part of FIG. 4.

FIG. 4 is a schematic diagram of a spectroscopy analyzer for real-time diagnostics of process according to another embodiment of the present invention, FIG. 5 is a schematic left side view of a main part of FIG. 4 and FIG. 6 is a schematic right side view of the main part of FIG. 4.

Referring to FIG. 4, the present invention includes a first gas receiving part 1110, a second gas receiving part 1120, a reactor 1130, an infrared ray emitting unit 1200, an infrared ray receiving unit 1300 and a calculating unit 1400.

The reactor 1130 may be one of the reactors 10 and 110 in the spectroscopy analyzer as shown in FIGS. 1 to 3. Therefore, as shown in FIG. 2, an input window 1131 and an output window 1132 are provided at a sidewall of the reactor 1130, and the input window 1131 and the output window 1132 may be the same as the input window 11, 111 and the output window 13, 116.

Referring to FIG. 4, the first gas receiving part 1110 is formed at an outer surface of the reactor 1130 so as to include a portion that the input window 1131 is provided, and the second gas receiving part 1120 is formed at an outer surface of the reactor 1130 so as to include a portion that the output window 1132 is provided. In other words, the first gas receiving part 1110 is formed at the outer surface of the reactor 1130 so that, when gas is injected into the first gas receiving part 1110, the injected gas can be contacted with the outer surface of the input window 1131, and the second gas receiving part 1120 is formed at the outer surface of the reactor 1130 so that, when the gas is injected into the second gas receiving part 1120, the injected gas can be contacted with the outer surface of the output window 1132. And the first and second gas receiving parts 1110 and 1120 are communicated with each other.

Referring to FIG. 4, the first and second gas receiving parts 1110 and 1120 are communicated with each other through lower ends thereof so that a recessed portion is formed between the first and second gas receiving parts 1110 and 1120. The reactor 1130 is settled in the recessed portion. Although not shown in drawings, the reactor 1130 is detachably settled in the recessed portion. For example, the reactor 1130 can be detached from the recessed portion by sliding on the recessed portion.

Referring to FIG. 4, an gas receiving part input window 1111 is disposed at the sidewall of the first gas receiving part 1110, and an gas receiving part output window 1122 is disposed at the sidewall of the second gas receiving part 1120. The gas receiving part input window 1111 is to introduce infrared ray generated from an infrared ray emitting unit 1200 provided at an outside of the first gas receiving part 1110 to the first gas receiving part 1110, and the gas receiving part output window 1122 is to output the infrared ray introduced to the second gas receiving part 1120 through the output window 1132 to the outside of the second gas receiving part 1120. The infrared ray emitting unit 1200 is a unit for generating the infrared ray introduced to the reactor 1130, and the infrared ray receiving unit 1300 is a unit for receiving the infrared ray passed through the reactor 1130.

Referring to FIGS. 5 and 6, the gas receiving part input window 1111 is formed to be larger than the input window 1131, and the gas receiving part output window 1122 is formed to be larger than the output window 1132. The infrared ray emitting unit 1200, the gas receiving part input window 1111, the input window 1131, the output window 1132, the gas receiving part output window 1122 and the infrared ray receiving unit 1300 are relatively positioned depending on the path of the infrared ray.

Referring to FIG. 4, the first gas receiving part 1110 has a length adjuster 1113 for adjusting a length of the first gas receiving part 1110, and the second gas receiving part 1120 has a length adjuster 1123 for adjusting a length of the second gas receiving part 1120. The length adjusters 1113 and 1123 function to control a volume of each of the first and second gas receiving parts 1110 and 1120. The length adjuster 1113, 1123 may be formed into a bellows portion, a sliding portion (not shown) or other shapes so as to control the volume of the first and second gas receiving parts 1110 and 1120.

Referring to FIG. 4, the first gas receiving part 1110 can be connected with a gas supplying part 1150 for supplying gas to the first gas receiving part 1110 and the second gas receiving part 1120. And, the gas supplying part 1150 has a gas inlet valve 1151 for controlling an amount of gas supplied to the first gas receiving part 1110 and the second gas receiving part 1120. Further, the gas supplying part 1150 may have a temperature control part 1154 for controlling a temperature of the gas supplied to the first gas receiving part 1110 and the second gas receiving part 1120, and the temperature control part 1154 may includes a heater for heating the gas received in the temperature control part 1154.

Referring to FIG. 4, a gas outlet valve 1162 for discharging the gas supplied to the first gas receiving part 1110 and the second gas receiving part 1120 may be connected to the second gas receiving part 1120, and a pump 1160 may be also connected to the gas outlet valve 1162. The pump 1160 is to discharge the gas to the outside and make vacuous in the first and second gas receiving parts 1110 and 1120 after the gas supplied from the gas supplying part 1150 to the first and second gas receiving parts 1110 and 1120 changes the temperature of the input and output windows 1131 and 1132 into a predetermined temperature.

Meanwhile, as shown in FIG. 4, the calculating unit 1400 is connected to the infrared ray receiving unit 1300. The calculating unit 1400 is a unit for processing data detected from the infrared ray receiving unit 1300 and analyzing the component of a chemical substance contained in the reaction byproduct or the reactant.

Hereinafter, an operation of the present will be described.

Referring to FIG. 4, it is preferred that the temperature of the input and output windows 1131 and 1132 provided at the reactor 1130 is the same as that of the reaction byproduct or the reactant. Therefore, in case of changing the temperature of the input and output windows 1131 and 1132, after the gas temperature of the gas supplying part 1150 is changed by the temperature control part 1154 to be same as that of the reaction byproduct or the reactant, the gas inlet valve 1151 is opened so that the gas is introduced into the first and second gas receiving parts 1110 and 1120. Then, the temperature of the input and output windows 1131 and 1132 becomes the same as that of the reaction byproduct or the reactant.

Referring to FIG. 4, if a desired time has passed after the gas is introduced in the first and second gas receiving parts 1110 and 1120, and it is determined that the temperature of the input and output windows 1131 and 1132 is sufficiently changed, the gas outlet valve 1162 is opened and the pump 1160 is driven so that the gas in the first and second gas receiving parts 1110 and 1120 is discharged to the outside. Therefore, the first and second gas receiving part 1110 and 1120 are maintained in the vacuum state. By this operation, information of the gas in the first and second gas receiving parts 1110 and 1120 is excluded, but information of the reaction byproduct or the reactant is analyzed by the infrared ray, since the spectroscopic analysis using the infrared ray is to obtain the information of the reaction byproduct or the reactant in the reactor 1130.

Referring to FIG. 4, if the first and second gas receiving parts 1110 and 1120 are maintained in the vacuum state, the reaction byproduct or the reactant is introduced in the reactor 1130.

If the reaction byproduct or the reactant is completely introduced in the reactor 1130, the infrared ray generated from the infrared ray emitting unit 1200 is injected into the reactor 1130 through the gas receiving part input window 1111 and the input window 1131, impacted to the reaction byproduct or the reactant and then collected in the infrared ray receiving unit 1300 through the output window 1132 and the gas receiving part output window 1122.

Referring to FIG. 4, the calculating unit 1400 connected with the infrared ray receiving unit 1300 processes the data detected from the infrared ray receiving unit 1300 and analyzes the component of the reaction byproduct or the reactant.

As shown in FIG. 4, since the reactor 1130 is detachably disposed between the first and second gas receiving parts 1110 and 1120, when the reactor 1130 is contaminated, there is an advantage that only the reactor 1130 can be facilely replaced.

In the embodiment of the present invention, the infrared ray emitting unit 1200 and the infrared ray receiving unit 1300 are provided at the outside of the first and second gas receiving parts 1110 and 1120. However, in other embodiment of the present invention, the infrared ray emitting unit 1200 and the infrared ray receiving unit 1300 may be provided in the first and second gas receiving parts 1110 and 1120. In this case, the gas receiving part input window 1111 and the gas receiving part output window 1122 are not provided.

In the embodiment of the present invention, the infrared ray is used. However, Raman, UV, laser and the like may be also used.

Figure 7:
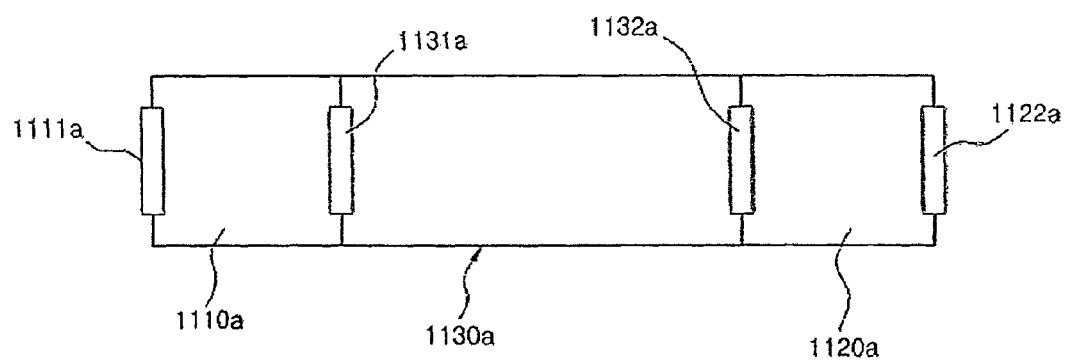
FIG. 7 is a schematic diagram of a main part of a spectroscopy analyzer for real-time diagnostics of process according to yet another embodiment of the present invention.

FIG. 7 is a schematic diagram of a main part of a spectroscopy analyzer for real-time diagnostics of process according to yet another embodiment of the present invention.

Referring to FIG. 7, like in the spectroscopy analyzer of FIG. 6, the present invention includes a reactor 1130a, an input window 1131a, an output window 1132a, a first gas receiving part 1110a, an gas receiving part input window 1111a, a second gas receiving part 1120a and an gas receiving part output window 1222a.

Unlike in the spectroscopy analyzer of FIG. 6, the first gas receiving part 1110a and the second gas receiving part 1120a are not communicated with each other. Therefore, although not shown in the drawing, it is preferred that gas supplied from one gas supplying part and having the same temperature is supplied to the first gas receiving part 1110a and the second gas receiving part 1120a. Further, it is preferred that a separate pump (not shown) for discharging the gas is connected to each of the first gas receiving part 1110a and the second gas receiving part 1120a.

INDUSTRIAL APPLICABILITY

According to the present invention, since the spectroscopic analysis is performed in vacuum state using the infrared ray, it is possible to precisely measure an intensity of the beam due to the refraction and scatter of the beam and thus it is facile to analyze the component of the reaction byproduct or the reactant.

Further, the measuring sensitivity can be improved by using the multi-path, and it can prevent contamination of an input window, an output window, a reflecting mirror, a crystal and the like by the reaction byproduct or the reactant, thereby extending the maintenance period and thus performing precisely performing the real-time diagnostics of process.

Further, since the gas is supplied between the first and second gas receiving parts, it is facile to control the temperature of the input and output windows corresponding to a temperature of the reaction byproduct or the reactant.

Furthermore, since the reactor is detachably disposed between the first and second gas receiving parts, when the reactor is contaminated, only the reactor 1130 can be facilely replaced.

In addition, since the present invention is provided with the pump for discharging the gas in the first and second gas receiving parts, the infrared ray output through the output window includes only the information of the reaction byproduct or the reactant.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A spectroscopy analyzer for real-time diagnostics of process, comprising:
   a reactor of which an internal portion becomes a vacuum state;
   a detector for detecting a beam output from the reactor; and
   an analyzer for performing quantitative and qualitative analysis of a sample using an intensity of the detected beam;
   wherein the reactor comprises,
   an input window through which the beam is introduced;
   a receiving part in which the beam introduced through the input window is injected, and a reaction byproduct or a reactant is received temporarily so as to perform the real-time diagnostics of the reaction byproduct or the reactant;
   an output window through which the beam injected in the receiving part is output after being refracted and scattered by the reaction byproduct or the reactant; and
   a reflecting mirror which is provided in the receiving part, and reflects the beam introduced through the input window to be reciprocated at last once in the receiving part and then outputs the beam.

2. The spectroscopy analyzer for real-time diagnostics of process as set forth in claim 1, wherein the reflecting mirror is disposed so that the beam introduced through the input window is reciprocated along a zigzag-shaped path in the receiving part.

3. The spectroscopy analyzer for real-time diagnostics of process as set forth in claim 2, wherein the receiving part is formed with a zigzag path for guiding a flow of the reaction byproduct or the reactant along the zigzag-shaped path of the introduced beam.

4. The spectroscopy analyzer for real-time diagnostics of process as set forth in claim 1, wherein the reactor further comprises a pressure controller for controlling pressure in the reactor.

5. The spectroscopy analyzer for real-time diagnostics of process as set forth in claim 1, further comprising an air curtain for injecting nitrogen gas so as to prevent the reaction byproduct or the reactant from being attached and deposited on the input window, the output window or the reflecting mirror.

6. The spectroscopy analyzer for real-time diagnostics of process as set forth in claim 1, wherein a temperature of the reactor can be controlled.

7. The spectroscopy analyzer for real-time diagnostics of process as set forth in claim 1, further comprising an injecting port for injecting gas or liquid so as to clean the sample attached and deposited on the input window, the output window or the reflecting mirror.

8. The spectroscopy analyzer for real-time diagnostics of process as set forth in claim 1, wherein the analyzer analyzes gas discharged from the reactor during a period of off-time and informs a cleaning period or a preliminary maintenance period.

9. The spectroscopy analyzer for real-time diagnostics of process as set forth in claim 1, further comprising:
   a first gas receiving part which is formed at an outer surface of the reactor so as to include a portion that the input window is provided, so that, when gas is injected into the first gas receiving part, the injected gas can be contacted with the outer surface of the input window; and
   a second gas receiving part which is formed at an outer surface of the reactor so as to include a portion that the output window is provided, so that, when gas is injected into the second gas receiving part, the injected gas can be contacted with the outer surface of the output window.

10. The spectroscopy analyzer for real-time diagnostics of process as set forth in claim 9, wherein the first gas receiving part and the second gas receiving part are communicated with each other.

11. The spectroscopy analyzer for real-time diagnostics of process as set forth in claim 10, further comprising an gas receiving part input window which is provided in the first gas receiving part so that a beam generated from an outside of the first gas receiving part can be injected into the first gas receiving part, and then be introduced through the input window; and an gas receiving part output window which is provided in the second gas receiving part so that the beam output through the output window can be output to an outside of the second gas receiving part.

12. The spectroscopy analyzer for real-time diagnostics of process as set forth in claim 11, wherein the first gas receiving part and the second gas receiving part are communicated with each other through lower ends thereof so that a recessed portion is formed between the first gas receiving part and the second gas receiving part, and the reactor is detachably disposed at the recessed portion.

13. The spectroscopy analyzer for real-time diagnostics of process as set forth in claim 11, further comprising a gas outlet valve which is connected to the first gas receiving part and the second gas receiving part; and a pump which is connected to the first gas receiving part and the second gas receiving part via the gas outlet valve.

14. The spectroscopy analyzer for real-time diagnostics of process as set forth in claim 11, further comprising a gas supplying part for supplying gas in the first gas receiving part and the second gas receiving part; and a temperature control part for controlling a temperature of the gas in the gas supplying part.

15. The spectroscopy analyzer for real-time diagnostics of process as set forth in claim 11, wherein a volume of one or all of the first gas receiving part and the second gas receiving part can be controlled.

16. The spectroscopy analyzer for real-time diagnostics of process as set forth in claim 15, wherein at least one of the first gas receiving part and the second gas receiving part has a length adjuster for adjusting a length thereof.

17. A spectroscopy analyzer for real-time diagnostics of process, comprising:

a reactor of which an internal portion becomes a vacuum state;

a detector for detecting refraction and scatter of a beam output from the reactor; and an analyzer for performing quantitative and qualitative analysis of a sample using an intensity of the detected beam;

wherein the reactor comprises, an input window through which the beam is introduced;

a receiving part in which the beam introduced through the input window is injected, and a reaction byproduct or a reactant is received temporarily so as to perform the real-time diagnostics of the reaction byproduct or the reactant;

a crystal which is fixedly provided in the receiving part by a fixing part so that the beam refracted and scattered by the reaction byproduct or the reactant can be passed therethrough;

a plasma electrode which is disposed to be apart from the crystal and provides continuous radiant rays in a far-infrared range; and an output window which outputs the beam output from the crystal.

18. The spectroscopy analyzer for real-time diagnostics of process as set forth in claim 17, further comprising a reflecting mirror which is provided in the receiving part so that the beam input through the input window is reciprocated at least once in the crystal and then output through the output window.

19. The spectroscopy analyzer for real-time diagnostics of process as set forth in claim 17, wherein the reactor further comprises a pressure controller for controlling pressure in the reactor.

20. The spectroscopy analyzer for real-time diagnostics of process as set forth in claim 17, further comprising a cleaning port for injecting inert gas so as to prevent attachment and deposition of the reaction byproduct or the reactant on the crystal and the plasma electrode.

21. The spectroscopy analyzer for real-time diagnostics of process as set forth in claim 17, wherein the fixing part can control a temperature of the crystal.

22. The spectroscopy analyzer for real-time diagnostics of process as set forth in claim 17, wherein the reactor further comprises an injecting port for injecting gas or liquid so as to clean the sample attached and deposited on the crystal and the plasma electrode, which is provided between the crystal and the plasma electrode.

23. A spectroscopy analyzer for real-time diagnostics of process, comprising:

a chemical reaction chamber in which a chemical reaction is occurred;

an input window which is provided at the chemical reaction chamber and through which a beam is introduced;

a crystal which is fixedly provided in the chemical reaction chamber by a fixing part so that the beam refracted and scattered by a reaction byproduct or a reactant in the chemical reaction chamber is passed therethrough;

a plasma electrode which is disposed to be apart from the crystal and provide continuous radiant rays in a far-infrared range;

an output window which is provided in the chemical reaction chamber so as to output the beam from the crystal;

a reflecting mirror which is provided in the chemical reaction chamber so that the beam input through the input window is reciprocated at least once in the crystal and then output through the output window;

a detector for detecting refraction and scatter of the beam output from the chemical reaction chamber; and an analyzer for performing quantitative and qualitative analysis of a sample using an intensity of the detected beam.

* * * * *